United States Patent [19]

Stephens et al.

[11] Patent Number: 5,136,107

[45] Date of Patent: Aug. 4, 1992

[54] PROCESS FOR HALOGENATING AROMATIC COMPOUNDS

[75] Inventors: Eddie M. Stephens; James C. Holly, both of Magnolia, Ark.

[73] Assignee: Ethyl Corporation, Richmond, Va.

[21] Appl. No.: 532,736

[22] Filed: Jun. 4, 1990

[51] Int. Cl.$^5$ ............................................. C07C 41/00
[52] U.S. Cl. ..................................... 568/639; 570/185
[58] Field of Search ........................... 568/639; 570/185

[56] References Cited

U.S. PATENT DOCUMENTS

| | | | |
|---|---|---|---|
| Re. 32,606 | 2/1988 | Stepniczka | 568/779 |
| 2,033,612 | 3/1936 | Clark et al. | 260/161 |
| 2,244,284 | 6/1941 | Britton et al. | 260/640 |
| 3,141,860 | 7/1964 | Sauer et al. | 260/33.8 |
| 3,232,959 | 2/1966 | Hahn et al. | 260/389 |
| 3,285,965 | 11/1966 | Jenkner | 260/612 |
| 3,331,797 | 7/1967 | Kopetz et al. | 260/28.5 |
| 3,578,716 | 5/1971 | Robinson | 568/639 |
| 3,752,856 | 8/1973 | Nagy et al. | 260/612 |
| 3,763,248 | 10/1973 | Mitchell | 260/649 |
| 3,833,674 | 9/1974 | Brackenridge | 260/649 |
| 3,911,033 | 10/1975 | Schaffner et al. | 260/649 |
| 3,959,387 | 5/1976 | Brackenridge | 260/612 |
| 3,965,197 | 6/1976 | Stepniczka | 260/623 |
| 4,072,658 | 2/1978 | Okamoto et al. | 260/49 |
| 4,287,373 | 9/1981 | Garman et al. | 568/639 |
| 4,521,633 | 6/1985 | Pedjac | 568/639 |
| 4,666,947 | 5/1987 | Brichta et al. | 521/79 |
| 4,701,564 | 10/1987 | Decaudin et al. | 568/639 |
| 4,717,776 | 1/1988 | Brackenridge et al. | 568/637 |
| 4,740,629 | 4/1988 | Brackenridge et al. | 568/639 |
| 4,766,253 | 8/1988 | Rauber | 568/639 |
| 4,814,525 | 3/1989 | Rule et al. | 570/203 |
| 4,849,547 | 7/1989 | Stollar et al. | 568/639 |

FOREIGN PATENT DOCUMENTS

| | | |
|---|---|---|
| 708209 | 4/1965 | Canada . |
| 0265150 | 4/1988 | European Pat. Off. . |
| 2521926 | 4/1976 | Fed. Rep. of Germany . |
| 2950877 | 6/1981 | Fed. Rep. of Germany . |
| 5173548 | 12/1974 | Japan . |
| 5239639 | 3/1977 | Japan . |
| 53-116332 | 10/1978 | Japan . |
| 3116333 | 10/1978 | Japan . |
| 3116334 | 10/1978 | Japan . |
| 5670060 | 4/1984 | Japan . |
| 981833 | 1/1965 | United Kingdom . |
| 991067 | 5/1965 | United Kingdom . |
| 1411524 | 10/1975 | United Kingdom . |
| 1472383 | 5/1977 | United Kingdom . |

OTHER PUBLICATIONS

"Flammfestmachen von Kunststoffen" by Dr. Hans Vogel, p. 49.
Inaba et al. in the J. Org. Chem., 49 (12), 2093–8, 1981.
Corey et al. J. Organomet. Chem. 210(2), 149–161, 1981.
Gassman et al. in J. Org. Chem., 47 (20), 4002–4, 1982.
CAS Registry Handbook, p. 632RL.
Chemical Abstracts, vol. 98, 1983 at 98:160866p.

*Primary Examiner*—Richard D. Lovering
*Assistant Examiner*—Joseph D. Anthony
*Attorney, Agent, or Firm*—David E. LaRose

[57] ABSTRACT

A process for producing a mixture of ar-brominated polyphenyl compounds with an average of from about 3 to about 4 bromine atoms per aromatic ring utilizing a novel catalytic system for at least a portion of the bromination reaction so as to obtain an ar-brominated polyphenyl compound with excellent color characteristics.

11 Claims, No Drawings

PROCESS FOR HALOGENATING AROMATIC COMPOUNDS

FIELD

This invention relates to a bromination process for aromatic hydrocarbons.

SUMMARY OF THE INVENTION

This invention relates to an improved process for the bromination of polyphenyl compounds such that the resulting product, which contains a mixture of brominated polyphenyl compounds, has improved color characteristics. Brominated polyphenyl compounds are to be understood as referring to ar-brominated polyphenyl compounds.

DETAILED DESCRIPTION

This invention relates to a process for the preparation of a mixture of brominated polyphenyl compounds having an average of about 3 to about 4 bromine atoms per aromatic ring, the process comprising: a) ar-brominating a polyphenyl compound so as to obtain a first mixture of brominated polyphenyl compounds having an average of from about 2 to about 3 bromine atoms per aromatic ring, at least a portion of the ar-bromination occurring in the presence of a catalytic system comprising a bromination catalyst and a catalyst moderator; and b) further ar-brominating the first mixture of brominated polyphenyl compounds to obtain a mixture of ar-brominated polyphenyl compounds having an average of from about 3 to about 4 bromine atoms per aromatic ring.

The ar-brominated polyphenyl compounds produced by the process of this invention consistently have superior color characteristics when compared to ar-brominated polyphenyl compounds made by other processes. When used as a flame retardant in thermoplastic formulations, the ar-brominated polyphenyl compounds of this invention do not contribute a substantial color component to articles made from such formulations.

In a preferred embodiment, this invention provides a process for the preparation of a mixture of ar-brominated diphenyl oxides having an average of from about 2 to about 5 bromine atoms per aromatic ring and having a white or near-white color, the process comprising: a) reacting bromine with diphenyl oxide to obtain a first mixture of brominated diphenyl oxides having an average of from about 0.5 to about 1.5 bromine atoms per aromatic ring; and b) subsequent to (a), further ar-brominating the first mixture by adding a bromination catalyst and additional bromine to the first mixture, at such a rate so as to form, in the presence of a catalyst moderator, the mixture of ar-brominated diphenyl oxides having a white or near-white color.

In another embodiment, this invention provides a process for the preparation of a mixture of ar-brominated diphenylethanes having an average of from about 2 to about 5 bromine atoms per aromatic ring and having a white or near-white color, the process comprising: a) reacting bromine with diphenylethane to obtain a first mixture of brominated diphenylethanes having an average of from about 0.5 to about 1.5 bromine atoms per aromatic ring; and b) subsequent to (a), further ar-brominating the first mixture by adding a bromination catalyst and additional bromine to the first mixture at such a rate so as to form in the presence of catalyst moderator the mixture of ar-brominated diphenylethanes having a white or near-white color.

The preferred polyphenyl compounds ar-brominated by the process of this invention are diphenylethane, diphenylmethane, diphenyl oxide, diphenylpropane, and polyphenyl ether. However, the process of this invention is not limited to the above polyphenyl compounds and may be adapted for use in the ring-bromination of other polyphenyl compounds.

At process initiation, a reaction vessel is initially charged with the quantity of polyphenyl compound to be ar-brominated. The polyphenyl compound may be charged as a solid or as a liquid to the reaction vessel. For ease of operation, the polyphenyl compound is preferably charged as a liquid, e.g. in a molten form. While charging the reaction vessel, the temperature of the polyphenyl compound is preferably maintained at least about 5° C. above its melting point to prevent freeze up in the feed conduit.

If it is desired to charge the polyphenyl compound as a liquid but not in the molten form, a suitable solvent can be used to form a solution with the polyphenyl compound. The solvent is preferably a non-reactive halogenated solvent and most preferably a halogenated aliphatic hydrocarbon. Suitable halogenated aliphatic hydrocarbons are ethylene dichloride, ethylene dibromide, methylene bromide, methylene chloride and the like. In a particular example, when the polyphenyl compound is diphenylethane, a suitable solvent is methylene bromide.

In accordance with the process of this invention, the obtainment of a mixture of ar-brominated polyphenyl compounds with good color characteristics is achieved by the use of a catalytic system for at least a portion of the ar-bromination of the polyphenyl compound. The catalytic system is comprised of a bromination catalyst and a catalyst moderator.

The bromination catalyst is preferably provided by a metal bromination catalyst or a metal halide bromination catalyst. Preferred metal halide bromination catalysts are the Lewis acid catalysts, which include $AlCl_3$, $AlBr_3$, $BBr_3$, $BCl_3$, $BF_3$, $FeCl_3$, $SbCl_5$, $SbCl_3$, $SnBr_4$, $SnCl_4$, $TiCl_4$, $UCl_4$, $ZnCl_2$, and $ZrCl_4$. Preferred metal bromination catalysts include Al, Fe, Ti, Zn, and Zr. When a metal bromination catalyst is used, the catalyst may be in the form of shavings, flakes, rings, saddles, beads, chunks, powder, and the like. In one preferred embodiment of the invention, diphenyl oxide is ar-brominated using an iron catalyst which is initially in the form of iron powder.

The total amount of catalyst added to the reaction mass is related to the amount of polyphenyl compound to be ar-brominated. Preferably the ratio of catalyst to polyphenyl compound ranges from about 0.0025 to about 0.125 moles of catalyst per 1 mole of polyphenyl compound. Most preferably, the ratio of catalyst to polyphenyl compound ranges from about 0.02 to about 0.0375 moles of catalyst per 1 mole of polyphenyl compound.

The catalyst moderator may be any organic or inorganic compound which is compatible with bromine and the polyphenyl compound to be ar-brominated. Suitable catalyst moderators are water, ethers, alcohols, and the like. Other compounds which may be useful as catalyst moderators are nitroalkanes and nitroarenes. A mixture of catalyst moderators may also be chosen depending on the particular polyphenyl compound to be ar-brominated and the bromination catalyst being used.

The amount of catalyst moderator is related to the amount of catalyst used. Preferably, the ratio of catalyst moderator to catalyst ranges from about 0.50 to about 10 moles of catalyst moderator per mole of catalyst. Most preferably, the ratio of catalyst moderator to catalyst ranges from about 1 to about 4 mole of catalyst moderator per mole of catalyst.

The catalytic system may be formed in situ during the ar-bromination of the polyphenyl compound, or it may be preformed prior to its addition to the reaction vessel. In a preferred embodiment the catalytic system is formed in situ by the addition of a bromination catalyst to the reaction vessel previously charged with a catalyst moderator. In a particularly preferred embodiment, the catalyst moderator is charged to the reaction vessel prior to charging the polyphenyl compound which is to be ar-brominated.

Once the polyphenyl compound has about 2 or more bromine atoms per aromatic ring, the use of the catalytic system of this invention is of less importance. Preferably, the catalytic system is used to obtain from about 1.5 to about 3 bromine atoms per aromatic ring and most preferably from about 2 to about 2.75 bromine atoms per aromatic ring. Subsequent to obtaining about 2.75 bromine atoms per aromatic ring, bromination of the polyphenyl compound may be performed in any conventional manner.

According to the process of this invention, the bromination of polyphenyl compounds is obtained by utilizing at least two steps. In the first step the polyphenyl compound is ar-brominated so as to obtain a first mixture of brominated polyphenyl compounds having an average of from about 2 to about 3 bromine atoms per aromatic ring. At least a portion of the ar-bromination in the first step should occur in the presence of a catalytic system. In the second step, the mixture of brominated polyphenyl compounds is further ar-brominated to obtain a mixture of ar-brominated polyphenyl compounds having an average of from about 3 to about 4 bromine atoms per aromatic ring.

In a preferred embodiment the polyphenyl compound is ar-brominated in at least three steps. In the first step, the polyphenyl compound is ar-brominated in the substantial absence of a bromination catalyst and/or catalytic system so as to obtain a mixture of ar-brominated polyphenyl compounds having an average of from about 0.5 to about 1.5 bromine atoms per aromatic ring. In the second step, the mixture is further ar-brominated so as to obtain a mixture of brominated polyphenyl compounds having an average of from about 1.5 to about 3 bromine atoms per aromatic ring, at least a portion of said further ar-bromination occurring in presence of the catalytic system. In the third step, the mixture obtained in the second step, is further ar-brominated so as to obtain a mixture of ar-brominated polyphenyl compounds having an average of from about 3 to about 4 bromine atoms per aromatic ring.

In the preferred embodiment, once the reaction vessel is charged with the quantity of polyphenyl compound, the polyphenyl compound is ar-brominated by adding a first portion of bromine and maintaining the reaction mass at a temperature and pressure for a period of time which is sufficient to ar-brominate the polyphenyl compound. The first portion of bromine, in the absence of a bromination catalyst and/or catalytic system, will partially ar-brominate the polyphenyl compound simply under the reaction conditions. The degree of partial ar-bromination will hold irrespective of the amount of excess bromine present. Thus, the first portion of bromine must provide, for bromination purposes, at least from about 0.5 to about 1.5 moles of bromine per aromatic ring in the polyphenyl compound. From a practical standpoint, the practitioner should not rely solely on theoretical amounts of bromine to be added as there will be bromine losses due to entrainment of bromine in the hydrogen bromine (HBr) vapors evolving from the reaction between bromine and the polyphenyl compound. It is preferable to use an amount of bromine which is substantially stoichiometric since a large excess of bromine, i.e. greater than about a 7% excess, may present a violent and uncontrollable bromination reaction when the bromination catalyst and/or catalytic system is used in the subsequent bromination of the polyphenyl compound.

Subsequent to obtaining the mixture having its average of from about 0.5 to about 1.5 bromine atoms per aromatic ring, further bromination is effected in the presence of a catalytic system and the addition of a sufficient amount of bromine to obtain from about 1.5 to about 3 bromine atoms per aromatic ring. To obtain more than 3 bromine atoms per aromatic ring, conventional bromination means are used, e.g. the addition of a bromination catalyst and sufficient bromine to obtain from about 3 to about 4 bromine atoms per aromatic ring.

Each time a bromination catalyst is called for, a different bromination catalyst may be selected. In a preferred embodiment, the same catalyst is utilized in each step and in equal amounts, though the use of the equal amounts of catalyst is not necessary, e.g., the first portion of catalyst added may be 1.5 to 2 times as much as the amount of catalyst added in the second and third portions.

When adding each portion of bromination catalyst, it may be added all at once, or over a period of time. The rate with which the catalyst is added is dependent on the ability to maintain the desired pressures and temperatures of the reaction mass during the catalyst addition. Preferably the catalyst is added as quickly as is possible keeping safety considerations in mind.

Preferably the bromination catalyst is added when there is substantially no ar-bromination occurring. The substantial cessation of the ar-bromination reaction can be determined by the amount of HBr evolving from the reaction mass. Those skilled in the art can readily determine when the ar-bromination reaction has substantially ceased.

The bromination of the polyphenyl compounds can be performed at temperatures ranging from about 50° C. to about 150° C. depending on the bromination catalyst and/or catalytic system which is used and the polyphenyl compound which is to be brominated. Preferably, the temperature ranges from about 70° C. to about 120° C. and most preferably from about 80° C. to about 110° C.

The pressure at which the bromination reaction is performed is not critical to the invention. Thus, the bromination reaction can be performed at atmospheric, subatmospheric, or superatmospheric pressures. Those skilled in the art can readily determine by conventional means the optimum pressure for ar-bromination of the polyphenyl compound.

The mixture of ar-brominated polyphenyl compounds produced by the process of this invention can be recovered and purified by any of several conventional methods. For example, steam can be introduced into the reaction vessel to heat the reaction mass to distill any remaining bromine therefrom and to form an aqueous mix. After the bromine has been removed, sodium carbonate is added to neutralize any acid that may be in the mix. Removal of catalyst from the neutralized mix is achieved by the addition of sodium gluconate or ethylenediaminetetraacetic acid tetrasodium salt ($Na_4EDTA$) which aids in the solubilization of the catalyst in the aqueous mix. Next, toluene or another organic solvent is added along with additional water to form an aqueous phase and an organic phase. The organic and aqueous phases are separated and the organic phase containing the product is distilled or stripped of toluene or organic solvent. Once these solvents are removed from the mixture, the product can be cooled until solidified and then broken or ground to the desired particle size.

An acceptable standard for determining the color of a product is provided by the use of the Hunter color values, "L", "a", and "b", which can be measured with a Hunter Spectro-colorimeter. The "L" value is a measure of lightness versus darkness or clearness versus cloudiness, with the higher values having greater lightness or clearness. The "a" and "b" values are measures of color. Positive "a" values indicate redishness, and negative "a" values indicate greenishness. Positive "b" values indicate yellowness and negative "b" values indicate bluishness.

The following examples are illustrative of the process of this invention.

EXAMPLE I

In a glass-lined reactor vessel equipped with a mechanical stirrer, a diptube, refrigerated condenser, and thermometer is placed about 1.9 grams of water and 793 grams of diphenyl oxide (DPO). Bromine (1,640 grams) is fed in slowly at 77° C. and 15 psig. The reaction mass is held at 77° C. for 30 minutes after the bromine feed is stopped or until an analysis of the sample indicates less than 7% free bromine and an average of 2 bromine atoms per mole of DPO. At this point the reactor is vented to atmospheric pressures and 1.5 grams of iron powder is added.

After adding the iron, an additional 965 grams of bromine is slowly fed into the reactor at a temperature of 77° C. while maintaining a reactor pressure of 15 psig. When all of the bromine has been added, the contents of the reactor are held at 77° C. for 15 minutes or until less than 7% free bromine, and an average of 3 bromine atoms per mole of DPO are obtained. At this point the reactor is again vented to atmospheric pressure and 2.5 grams of iron powder are added.

Bromine (1,140) grams is then fed in slowly at 77°-104° C. at 15 psig. After feeding in bromine, the reactor is held at 104° C. for 15 minutes or until there is less than 8% free bromine and an average of 4.5 bromine atoms per mole of DPO. After venting to the atmosphere 2 grams of iron powder are added to the reactor. Bromine (2,080 grams) is fed in slowly at a temperature of 104°-114° C. and 15 to 30 psig.

At the end of the bromine feed cycle, any free bromine is stripped by sparging with steam for 3 to 6 hours at a temperature of 129°-140° C. Sodium gluconate (25 grams) and 25 grams of sodium carbonate are added followed by 1,190 grams of toluene, then 540 grams of water. After stirring well, the water is separated and the organic layer washed two more times with about 540 grams of water.

The toluene is then removed by distillation through a wiped film evaporator at 300 mm absolute pressure and 121° C., leaving an oil that solidifies on cooling.

Following the above general procedure, the product homolog distribution as measured by gas chromotography (GC) was as follows:

| Product Homolog | CG Area % |
| --- | --- |
| $Br_6$ | 9.4 |
| $Br_7$ | 44.3 |
| $Br_8$ | 36.9 |
| $Br_9$ | 8.8 |
| $Br_{10}$ | 0.6 |

To determine the Hunter color values, the product was dissolved in toluene such that a mixture of approximately 50 wt. % product and 50% wt. % toluene was obtained. The dissolved product was then placed in a 50 mm cell of a Hunter Labscan spectrocolorimeter. Samples with "a" values higher than about 5 are considered less desirable since they have a reddish color which can be imparted to thermoplastic resin formulations of which they are a part.

The Hunter "a" values were as follows:

| Sample | Hunter "a" value |
| --- | --- |
| 1 | 1.8 |
| 2 | 2.0 |

EXAMPLE II

Samples 3-8 were produced by the general procedure of Example I, except that iron powder was added in three equal portions to the reactor. The Hunter "a" value were as follows:

| Sample | Hunter "a" value |
| --- | --- |
| 3 | 1.4 |
| 4 | 2.8 |
| 5 | 1.9 |
| 6 | 2.8 |
| 7 | 3.9 |
| 8 | 3.6 |

EXAMPLE III

Samples 9 and 10 were produced by the general procedure of Example I except that the iron powder was added in two portions with the first portion being twice as much as the second portion and bromine was continuously fed in after the second portion of iron was added until the desired bromine number was achieved.

| Sample | Hunter "a" Value |
| --- | --- |
| 9 | 2.9 |
| 10 | 3.5 |

EXAMPLE IV

Samples 11 and 12 were produced by the general procedure of Example III except that the iron was added in two equal portions.

| Sample | Hunter "a" value |
|---|---|
| 11 | 5.6 |
| 12 | 6.0 |

EXAMPLE V

In a 1 liter, round bottomed flask equipped with a mechanical stirrer, addition funnel, refrigerated condenser, and thermometer was placed 101.3 grams of diphenyl oxide. Bromine (67 mL) was added to the diphenyl oxide which was initially at 30° C. over a period of about 50 minutes. The temperature rose slowly to 60° C. during the addition and was held at 55°-65°C. throughout the bromine addition. The reaction mass was held for 10 minutes at 60°-65° C. and then 0.35 mL of methanol was added followed by 0.2 grams of iron powder. A second portion of bromine (50 mL) was then added dropwise over a period of 45 minutes to the reaction mass which was at 70-85 C. Then an additional 0.2 grams of iron powder was added. A third portion of bromine (46 mL) was then added slowly over a period of 40 minutes to the reaction mass which now had a temperature of 75°-100° C. The reaction mass was held at 100° C. for 15 minutes then a third portion of iron powder (0.4 grams) was added and the temperature of the reaction mass was raised to 110° C. A fourth portion of bromine (68 mL) was then added dropwise over 2 hours and 15 minutes to the reaction mass which was held at 110°-115° C. A sample taken at this point indicated an average bromine number of 7.09. An additional 10 mL of bromine was added in 15 minutes and the reaction mass was held at 110°-115° C. for 40 minutes. At this point, the average bromine number was 7.38. Fifteen minutes later, 30 mL of water was added to the reaction mass and the reaction mass was held at 100°-115° C. until most of the bromine was removed from the reaction mass.

After the bromine was removed from the reaction mass, 6 grams of ethylenediaminetetracetic acid tetrasodium salt (Na$_4$EDTA) and 10.6 grams of sodium carbonate were added followed by 224 grams of toluene and 200 mL of water. The mix was stirred well at 80°-85° C. then phase separated. The organic layer containing the product was washed with 200 mL of hot water phase separated again. The product remained in the organic layer.

Hunter values were as follows:

| Hunter Values |
|---|
| L = 97.6 |
| a = 0.00 |
| b = 5.9 |

The product produced as a result of this invention was water white or near white in solution rather than reddish or brown as with other processes. In comparison, a mixture of brominated diphenyl oxides having an average of about 3.6 to about 3.9 bromine atoms per aromatic ring made by a previous process has an average Hunter "a", value of from about 6 to about 9 or higher.

EXAMPLE VI

In a 1-liter, round bottom flask equipped with a mechanical stirrer, addition funnel, refrigerated condenser, and thermometer was placed 97.3 grams of diphenyl oxide, 0.21 grams of iron and 0.23 mL of water. Bromine (70 mL) was slowly added to the mixture which was initially at 35° C. and the temperature rose quickly to 55°-60 C. and was held there during the period of bromine addition time. The temperature was then increased to 75°-80° C. and held there until a total of 103 mL of bromine had been added. After holding the mixture at 75° C. until there was no evidence of bromine vapor in the reactor, an additional 30 mL of bromine was added at 75° C. in about 15 minutes. A sample of the reaction mass after 15 minutes indicated 7 weight percent free bromine and an average of about 2 bromine atoms per aromatic ring. A second portion of iron powder (0.57 grams) was added followed by additional bromine as the temperature rose to 110°-115° C. When 90 mL of additional bromine had been added, the mixture was held at 110°-115° C. for 40 minutes and a sample indicated an average of about 3.5 bromine atoms per aromatic ring. An additional 10 mL of bromine was added and the reaction mass was held for one hour at 110°-115° C. A sample at the end of this time indicated an average of about 3.6 bromine atoms per aromatic ring. Bromine (5 mL) was added and the temperature was held at 110°-115° C. for an additional hour at which time analysis showed an average of about 3.72 bromine atoms per aromatic ring. Water was then added to kill any further reaction and the product was purified by the general procedure of Example 1. Hunter values for the recovered product were as follows:

| Hunter Values |
|---|
| L = 96.66 |
| a = −0.49 |
| b = 8.1 |

Mixtures of brominated polyphenyl compounds are useful as flame retardants in a wide variety of organic material such as polyethylene, polypropylene, polyesters, acrylonitrilebutadienestyrene terpolymer, styrene, high impact polystyrene, styrenebutadiene copolymer, styrene-maleic anhydride copolymer, polyphenylene ethers and blends of the above. The amount used is generally an amount to provide about 5-15 weight percent bromine to the polymer. Synergists, such as antimony oxide, are routinely included.

While the foregoing description contemplates a batch reaction system, the use of a semi-continuous or a continuous process is to be understood to be within the spirit and scope of the claimed invention.

What is claimed is:

1. In a process for preparing a mixture of brominated diphenyl oxides having an average of about 2 to about 5 bromine atoms per ring by charging a reaction vessel with diphenyl oxide, bromine, bromination catalyst, and a catalyst moderator, the improvement therein which comprises adding bromine and said bromination catalyst incrementally over time to the mixture of diphenyl oxide and catalyst moderator, thereby accurately controlling the degree of bromination and decreasing the Hunter color value "a" of the brominated product to a value less than 5.

2. The process of claim 1 wherein said bromination catalyst is selected from the group consisting of iron and iron bromide.

3. The process of claim 2 wherein said bromination catalyst is iron powder.

4. The process of claim 3 wherein the ratio of said bromination catalyst to diphenyl oxide ranges from about 0.0025 to about 0.125 moles of catalyst per mole of diphenyl oxide.

5. The process of claim 1 wherein said catalyst moderator is selected from the group consisting of water and methanol.

6. The process of claim 5 wherein said catalyst moderator is water.

7. The process of claim 6 wherein the ratio of said catalyst moderator to said bromination catalyst ranges from about 0.50 to about 10 moles of catalyst moderator per mole of bromination catalyst.

8. The process of claim 1 wherein said bromination catalyst is iron powder and said catalyst moderator is water.

9. The process of claim 1 wherein said bromination catalyst is added in two or more increments.

10. The process of claim 9 wherein said bromination catalyst is added in three increments.

11. A process for preparing a mixture of brominated diphenyl oxides having an average bromine number between 6 and 8 which comprises charging a reaction vessel with diphenyl oxide, water, and sufficient bromine to produce a brominated diphenyl oxide having an average bromine number between 1 and 3, thereafter adding iron powder and additional bromine incrementally over time until the desired bromine number is achieved, yielding brominated diphenyl oxide having a Hunter value "a" which is less than 5.

* * * * *